US00PP16355P3

(12) United States Plant Patent

Ishihara et al.

(10) Patent No.: US PP16,355 P3
(45) Date of Patent: Mar. 21, 2006

(54) *PETUNIA* PLANT NAMED 'SUNCOPABLUE'

(50) Latin Name: *Petunia hybrida*
Varietal Denomination: Suncopablue

(75) Inventors: Takuro Ishihara, Higashikurume (JP); Kazunari Iwaki, Omihachiman (JP); Kiyoshi Miyazaki, Hikone (JP); Shinya Miyano, Katori-gun (JP)

(73) Assignees: Suntory Flowers Limited, Tokyo (JP); Keisei Rose Nurseries, Inc., Tokyo (JP)

( * ) Notice: Subject to any disclaimer, the term of this patent is extended or adjusted under 35 U.S.C. 154(b) by 136 days.

(21) Appl. No.: 10/811,242

(22) Filed: Mar. 25, 2004

(65) Prior Publication Data

US 2005/0217000 P1 Sep. 29, 2005

(51) Int. Cl.
*A01H 5/00* (2006.01)

(52) U.S. Cl. ..... Plt./356
(58) Field of Classification Search ..... Plt./356
See application file for complete search history.

(56) References Cited

U.S. PATENT DOCUMENTS

| | | | | |
|---|---|---|---|---|
| PP6,899 P | | 7/1989 | Tsuda et al. | |
| PP6,914 P | | 7/1989 | Tsuda et al. | |
| PP6,915 P | | 7/1989 | Tsuda et al. | |
| PP9,322 P | | 10/1995 | Tachibana et al. | |
| PP15,113 P2 | * | 8/2004 | Strope | Plt./356 |

FOREIGN PATENT DOCUMENTS

| | | |
|---|---|---|
| JP | PBR 8036 | 3/2000 |

OTHER PUBLICATIONS

Germania Seed Homepage http://www.germaniaseed.com.*
Suntory Collection and Other Specialty Annuals http://www.germaniaseed.com/pdf/04–747Pineae.pdf.*
UPOV ROM GTITM Computer Database, GTI Jouve Retrieval Software 2004/06 Citation for 'Suncopablue'.*
Explanation of Publication of Japanese PBR Registration.
Explanation for IDS Documents.
Suntory Flowers Ltd., "Flower & Green, the newest catalog 2004" Published 2003.
Jackson & Perkins Wholesale, Inc., USA, "The 2004 Suntory Collection" Published 2003.
Pineae Greenhouses, Inc., USA, "Pineae Peak Performers featuring the 2004 Suntory COLLECTION" Published 2003.
Goldsmith Seeds, Inc., USA, "Goldsmith Seeds 2003–2004 Catalog" Published 2003.
Sakata Seeds Co., Japan, "Katei Engei, 2004 Spring" Published 2003.
Fukukaen Nursery & Bulb Co., Ltd., Japan, "FUKUKAEN Flower Catalogue for Gardening Farm, Autumn 2003 to Spring 2004" Published 2003.
Dai–ichi Seed Co., Ltd., Japan, "Dai–ichi Seed Co., Ltd. Catalogue for Gardening Farm, Summer 2000 to Spring 2001" Published 1999.

* cited by examiner

*Primary Examiner*—Kent Bell
*Assistant Examiner*—W. C. Haas
(74) *Attorney, Agent, or Firm*—Christie, Parker and Hale, LLP

(57) ABSTRACT

Disclosed herein is a new and distinct variety of *Petunia* plant having a decumbent habit and short stems. The *Petunia* plant has abundant branching, and a great profusion of blooms, the whole plant remaining in bloom for a considerable period of time. The flowers are single and small, the petals having vivid purple color. The inside color of the corolla throat is brilliant purple and the outside of the corolla tube is moderate purple. The plant exhibits high resistance to heat, cold, rain and disease.

2 Drawing Sheets

Botanical designation: *Petunia hybrida.*
Variety denomination: 'Suncopablue'.

BACKGROUND OF THE VARIETY

The present invention relates to a new and distinct variety of *Petunia* plant originated from crossing of a seedling called 'Fantasy Blue' (unpatented) as the female parent and a *Petunia* hybrid variety called 'PAB2' (unpatented) as the male parent.

The *Petunia* is a very popular plant that is used for flower bedding and potting in the summer season. There are only a few *Petunia* varieties known to the inventors which do not have an upright growth habit and which have a high resistance to rain, heat, and disease. *Petunias* of the 'Revolution' series include 'Revolution Purple pink' (U.S. Plant Pat. No. 6,915), 'Revolution Brillant pink' (U.S. Plant Pat. No. 6,914), 'Revolution Brillantpink-Mini' (U.S. Plant Pat. No.

6,899), and 'Revolution Blue vein' (U.S. Plant Pat. No. 9,322). These are decumbent type plants having long stems, a low plant height, abundant branching, and a high resistance to heat, rain and disease. However, there are only a few *Petunia* varieties known to the inventors having a decumbent and compact plant shape, a great profusion of small size flowers, vivid purple petals and a high resistance to rain, heat, and disease. Accordingly, this invention was aimed at obtaining a new *Petunia* variety having vivid purple petals, together with the above features.

The female parent 'Fantasy Blue' used in the crossing that created 'Suncopablue' is a cultivar, having an erect growth habit with many branches. It has small single flowers, the petals having vivid violet color. The seed of 'Fantasy Blue' was bought from Sakata Seed Corp. The growth habit of the female parent 'Fantasy Blue' is erect. In contrast, that of 'Suncopablue' is decumbent.

The male parent 'PAB2' used in the crossing that created 'Suncopablue' is a strain of our breeding lines, having a decumbent growth habit with many branches. It has small single flowers, the petals having a violet color. The spreading area of 'PAB2' is smaller than that of 'Suncopablue'.

In July 2000, crossing of 'Fantasy Blue' as the female parent and 'PAB2' (unpatented) as the male parent was conducted at Yokaichi-shi, Shiga-ken, Japan. In April 2001, 80 seedlings were obtained from that crossing. These seedlings were grown in pots in glasshouses and were evaluated. One seedling was selected in view of its growth habit, flower size and color in September 2001. That seedling was propagated by cutting and a trial was carried out by flower potting and bedding from April to September 2002 at Yokaichi-shi, Shiga-ken, Japan. The botanical characteristics of that plant were then examined, using similar varieties 'Revolution Violet-mini' (unpatented), and 'Fantasy Crystal Red' (unpatented) for comparison. As a result, it was concluded that this *Petunia* plant is distinguishable from any other variety, whose existence is known to us, and is uniform and stable in its characteristics. Then the new variety of *Petunia* plant was named 'Suncopablue'.

In the following description, the color-coding is in accordance with The R.H.S. Colour Chart.

SUMMARY OF THE VARIETY

This new variety is unlike any *Petunia* commercially available, known to the inventors, as evidenced by the following unique combinations of characteristics.

1. Rather compact and decumbent growth habit with short stems.
2. Having abundant branching and a great profusion of blooms.
3. The flowers are single and small. The petal color is vivid purple (R.H.S.N87A).
4. The plant has a high resistance to rain, cold, heat and disease.

The new variety 'Suncopablue' differs from the similar variety 'Revolution Violet-mini' in the following points.

1. The spreading area of 'Suncopablue' is smaller than that of 'Revolution Violet-mini'.
2. The stem length of 'Suncopablue' is shorter than that of 'Revolution Violet-mini'.
3. The internode length of 'Suncopablue' is shorter than that of 'Revolution Violet-mini'.
4. The flower size of 'Suncopablue' is smaller than that of 'Revolution Violet-mini'.

The new variety 'Suncopablue' differs from the similar variety 'Fantasy Crystal Red' in the following points.

1. The growth habit of 'Suncopablue' is decumbent. That of 'Fantasy Crystal Red' is erect.
2. The spreading area of 'Suncopablue' is larger than that of 'Fantasy Crystal Red'.
3. The stem length of 'Suncopablue' is shorter than that of 'Fantasy Crystal Red'.
4. The leaf of 'Suncopablue' is thinner than that of 'Fantasy Crystal Red'.
5. The petal color of 'Suncopablue' is vivid purple (R.H.S.N87A). That of 'Fantasy Crystal Red' is vivid red (R.H.S.52A) with strong red (R.H.S.53C) vein.
6. The apex shape of petal of 'Suncopablue' is rounded. That of 'Fantasy Crystal Red' is obtuse.
7. The petal lobatin of 'Suncopablue' is shallower than that of 'Fantasy Crystal Red'.
8. The heat resistance of 'Suncopablue' is stronger than that of 'Fantasy Crystal Red'.

The new variety of *Petunia* plant 'Suncopablue' was asexually reproduced by the use of cuttings at Yokaichi-shi, Shiga-ken, Japan, and homogeneity and stability thereof were confirmed. The instant plant retains its distinctive characteristics and reproduces true to type in successive generations.

BRIEF DESCRIPTION OF THE PHOTOGRAPH

The depicted plants had been reproduced by the use of cuttings and were photographed during July 2003 while cultivating under the trial field in 15 cm pots at an age of approximately 6 months at Yokaichi-shi, Shiga, Japan.

DESCRIPTION OF THE VARIETY

Figure 1:
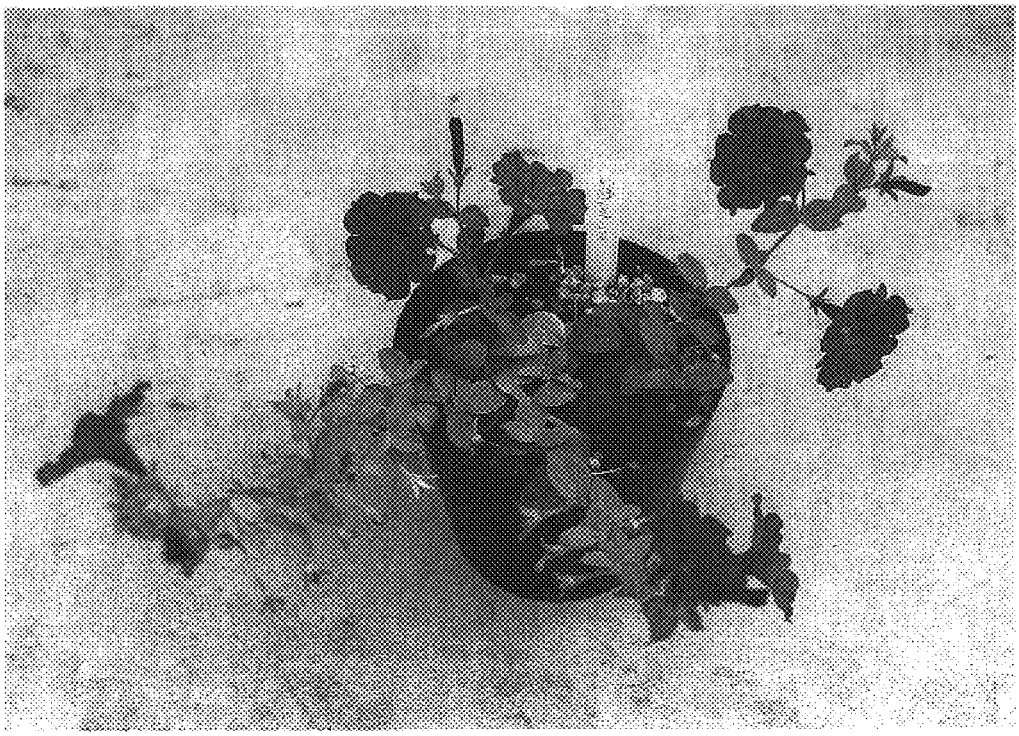
FIG. 1 illustrates a typical plant of the new variety of *Petunia* plant 'Suncopablue' while growing in a pot.
Figure 2:
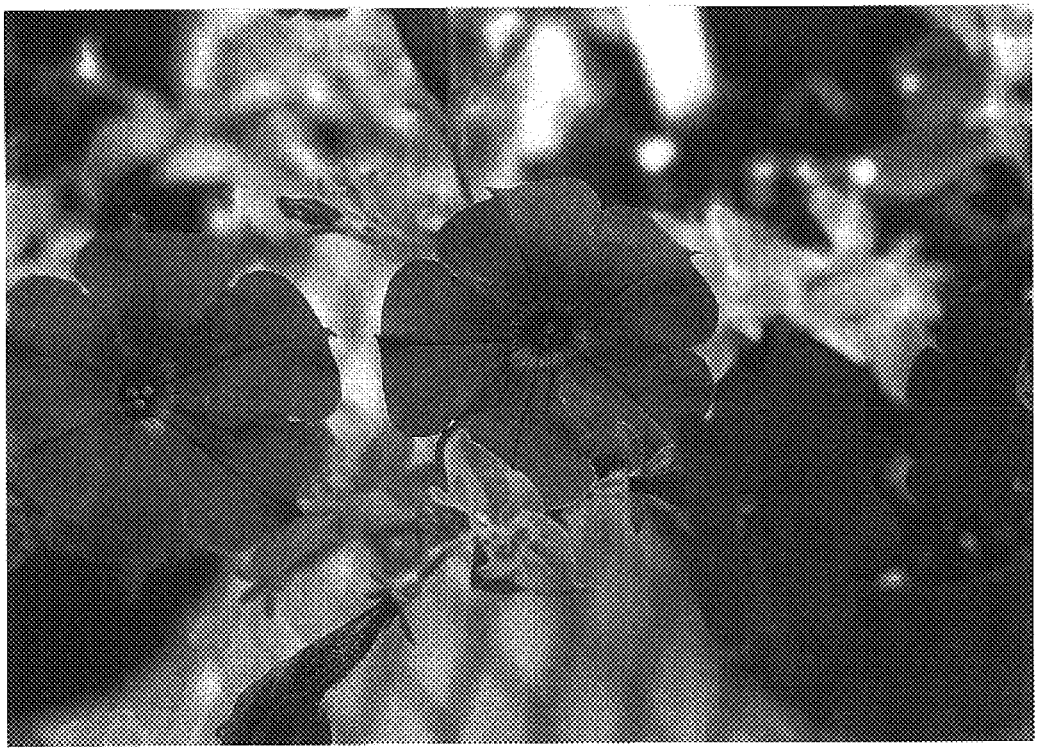
FIG. 2 illustrates a close view of typical foliage and blossoms of the new variety of *Petunia* plant 'Suncopablue'.

The botanical characteristics of the new and distinct variety of *Petunia* plant named 'Suncopablue' are as follows when observed as grown in typical outdoor conditions during July at Yokaichi-shi, Shiga-ken, Japan, at an age of approximately 6 months. The average day temperature is approximately 22° C. and the average night temperature is approximately 13° C.

Plant:

*Growth habit.*—Decumbent.
*Plant height.*—Approximately 15.6 cm.
*Spreading area of plant.*—Approximately 26.0 cm.
*blooming period.*—Early April to late October in the southern Kanto area, Japan. The plant shape does not change throughout this period. A typical flower commonly lasts approximately 5 days on the plant when experiencing a temperature of approximately 20° C.

Stem:

*Length.*—Approximately 2.4 cm.
*Diameter.*—Approximately 1.5 mm.
*Pubescence.*—Present and typical of the species.
*Branching.*—Approximately 4 branches per plant.
*Internode length.*—Approximately 2.1 cm.
*Color.*—R.H.S. 144A (strong yellow green).

Leaf:

*Whole shape.*—Elliptic with entire margin. The apex shape is acute, and the base shape is attenuate.
*Length.*—Approximately 3.2 cm.
*Width.*—Approximately 2.2 cm.
*Color.*—Upper side color is R.H.S. 144B (vivid yellow green). Lower side color is R.H.S. 146C (moderate yellow green).
*Thickness.*—Approximately 0.2 mm.
*Pubescence.*—Sparse.

Flower:

*Facing direction.*—Slanted upward.
*Type.*—Single.
*Shape.*—Funnel-shaped, with five-fissures.
*Shape of petal tip.*—Rounded.
*Lobation.*—Shallow.
*Waving of petal.*—Weak.
*Flower diameter.*—Approximately 4.4 cm.
*Flower depth.*—Approximately 3.0 cm.

*Flower color.*—Upper Petal Surface Color: near R.H.S. 87A. Lower Petal Surface Color: near R.H.S. 87C. Inside color of flower throat: R.H.S. N81C. Outside color of flower tube: R.H.S. 83B.

*Calyx.*—Narrow. 5 sepals fused at the base. Diameter: Approximately 15 mm. Depth: Approximately 10 mm. Color (upper and lower surfaces): near R.H.S. 144B. Texture (both surfaces): Smooth.

*Reproductive organs.*—1 normal pistil and 5 normal stamens. Color of pistil is R.H.S. 15C (light yellow green). Color of stamen is R.H.S. 150D (pale yellow green).

*Peduncle.*—Diameter: Approximately 0.8 mm. Length: Approximately 1.8 cm. Color: near R.H.S. 144A. Texture: Smooth.

Physiological and ecological characteristics: High resistance to cold, rain, heat and disease. Moderate resistance to pests. 'Suncopablue' has a low temperature tolerance of at least 5° C.

Seed population has not been observed.

This new variety of *Petunia* plant is most suitable for flower bedding and potting, particularly in hanging pots or planters. Pinching of old blossoms will enhance the formation of new blossoms.

It is claimed:

1. A new and distinct variety of *Petunia* plant named 'Suncopablue', substantially as herein illustrated and described.

* * * * *